United States Patent [19]

Sugimori et al.

[11] Patent Number: 4,659,501
[45] Date of Patent: Apr. 21, 1987

[54] 2-CYANO-4-HALOGENOPHENYL SUBSTITUTED-BENZOATES

[75] Inventors: Shigeru Sugimori, Fujisawashi; Toyoshiro Isoyama; Yasuyuki Goto, both of Yokohamashi, all of Japan

[73] Assignee: Chisso Corporation, Kitaku, Japan

[21] Appl. No.: 692,166

[22] Filed: Jan. 17, 1985

[30] Foreign Application Priority Data

Jan. 30, 1984 [JP] Japan ................................ 59-14767
Mar. 14, 1984 [JP] Japan ................................ 59-48372
Mar. 19, 1984 [JP] Japan ................................ 59-52483

[51] Int. Cl.⁴ .................... C09K 19/54; C09K 19/30; C09K 19/20; C07C 121/52
[52] U.S. Cl. .................. 252/299.5; 252/299.63; 252/299.64; 252/299.1; 558/416; 350/350 R; 350/349; 350/346
[58] Field of Search .......... 252/299.63, 299.5, 299.64, 252/299.67, 299.1; 260/465 G, 465 K, 465 R; 558/416; 350/346, 350 R, 349

[56] References Cited

U.S. PATENT DOCUMENTS

| | | | |
|---|---|---|---|
| 3,915,883 | 10/1975 | Van Meter et al. | 252/299.64 |
| 3,953,491 | 4/1976 | Steinstrasser et al. | 252/299.64 |
| 4,147,656 | 4/1979 | Aldrich et al. | 252/299.64 |
| 4,293,434 | 10/1981 | Deutscher et al. | 252/299.63 |
| 4,368,135 | 1/1983 | Osman | 252/299.63 |
| 4,400,293 | 8/1983 | Romer et al. | 252/299.63 |
| 4,502,974 | 3/1985 | Sugimori et al. | 252/299.63 |

FOREIGN PATENT DOCUMENTS

| | | | |
|---|---|---|---|
| 19665 | 12/1980 | European Pat. Off. | 252/299.63 |
| 2655890 | 6/1978 | Fed. Rep. of Germany | 252/299.64 |
| 2181943 | 1/1974 | France | 252/299.64 |
| 55-84385 | 6/1980 | Japan | 252/299.64 |
| 1432692 | 4/1976 | United Kingdom | 252/299.64 |
| 2,111,974 | 7/1983 | United Kingdom | 252/299.63 |

Primary Examiner—Teddy S. Gron
Assistant Examiner—J. E. Thomas
Attorney, Agent, or Firm—Wenderoth, Lind & Ponack

[57] ABSTRACT

Novel liquid crystal compounds, 2-cyano-4-halogenophenyl substituted-benzoates suitable as a component constituting a liquid crystal composition which exhibits a negative dielectric anisotropy, and a liquid crystal composition containing the same are provided, which benzoates are expressed by the formula

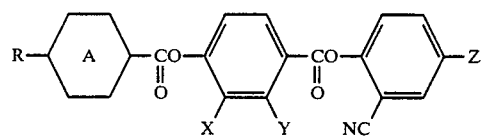

wherein R represents an alkyl group or an alkoxy group each of 1 to 10 carbon atoms;

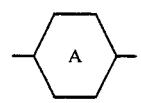

represents

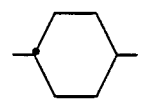

or

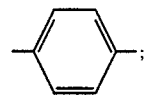

X and Y each represents H or a halogen atom of F or Cl and at least one of X and Y is necessarily H; and Z represents a halogen atom of F, Cl or Br.

9 Claims, No Drawings

2-CYANO-4-HALOGENOPHENYL SUBSTITUTED-BENZOATES

BACKGROUND OF THE INVENTION

This invention relates to novel liquid crystal compounds having a large negative dielectric anisotropy and useful as a component of liquid crystal compositions, and also to a liquid crystal composition containing the same.

Display elements having liquid crystals applied therein utilize the optical anisotropy and dielectric anisotropy of liquid crystal substances, and they are classified into various modes such as those of TN type (twisted nematic type), DS type (dynamic scattering type), guest-host type, DAP type, etc. depending on their display modes, and there vary the properties of liquid crystal substances suitable to use for the respective modes. Liquid crystals for the above uses are required to have common properties that they are stable to moisture, air, heat, light, etc., and those have been desired which exhibit liquid-crystalline phases within a temperature range as broad as possible, centered around room temperature.

At present, there is no compound which alone satisfies such conditions; hence liquid crystal compositions obtained by mixing several kinds of liquid crystal compounds or these compounds together with non-liquid-crystalline compounds have been used.

Recently, guest-host type liquid crystal display elements in one of color liquid crystal display modes have come to be particularly noted. The elements use a mixture of liquid crystals with a dyestuff, and liquid crystal materials having a negative dielectric anisotropy are used in positive type guest-host mode display elements. Thus, as a component constituting the liquid crystal composition, a liquid crystal compound has been required which has a negative value of dielectric anisotropy the absolute value of which is as large as possible, and also has a low viscosity and a superior compatibility.

SUMMARY OF THE INVENTION

The object of the present invention is to provide a novel liquid crystal compound suitable as a component constituting a liquid crystal composition which exhibits a negative dielectric anisotropy, and a liquid crystal composition containing the same.

The present invention resides, in one aspect, in
(1) 2-cyano-4-halogenophenyl substituted-benzoates expressed by the formula

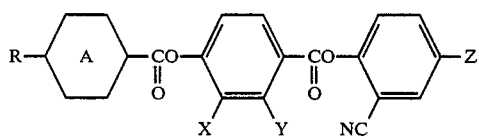
(I)

wherein R represents an alkyl group or an alkoxy group each of 1 to 10 carbon atoms;

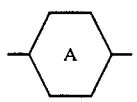

represents

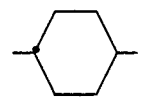

or

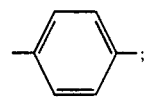

X and Y each represent H or a halogen atom of F or Cl and at least one of X and Y is necessarily H; and Z represents a halogen atom of F, Cl or Br.

The embodiments of the above item (1) consist in the following items (2)~(7):
(2) 2-Cyano-4-halogenophenyl 4-(trans-4-substituted cyclohexylcarbonyloxy)benzoates according to the above item (1) and expressed by the formula

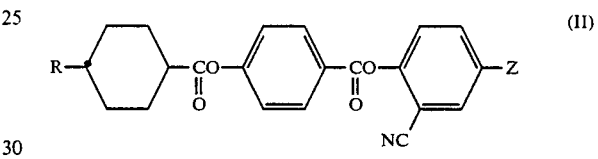
(II)

wherein R and Z are as defined above.
(3) 2-Cyano-4-halogenophenyl 4-(4-substituted benzoyloxy)-benzoates according to the above item (1) and expressed by the formula

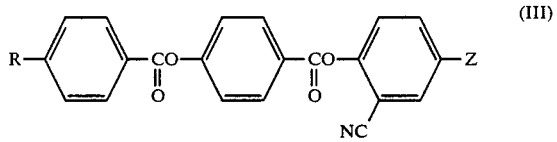
(III)

wherein R and Z are as defined above.
(4) 2-Cyano-4-halogenophenyl 2-halogeno-4-(trans-4-substituted cyclohexylcarbonyloxy)benzoates according to the above item (1) and expressed by the formula

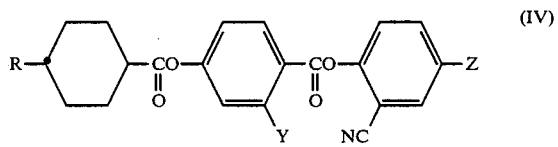
(IV)

wherein R and Z are as defined above and Y represents F or Cl.
(5) 2-Cyano-4-halogenophenyl 2-halogeno-4-(4-substituted benzoyloxy)benzoates according to the above item (1) and expressed by the formula

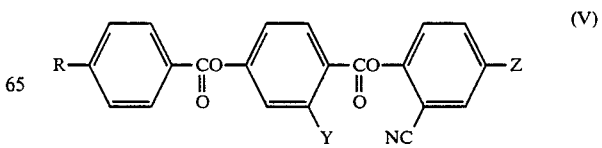
(V)

wherein R and Z are as defined above and Y represents F or Cl.

(6) 2-Cyano-4-halogenophenyl 3-halogeno-4-(trans-4-substituted cyclohexylcarbonyloxy)benzoates according to the above item (1) and expressed by the formula

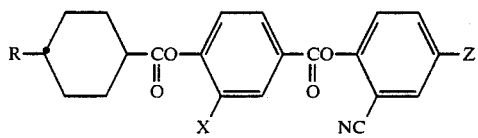
(VI)

wherein R and Z are as defined above and X represents F or Cl.

(7) 2-Cyano-4-halogenophenyl 3-halogeno-4-(4-substituted benzoyloxy)benzoates according to the above item (1) and expressed by the formula

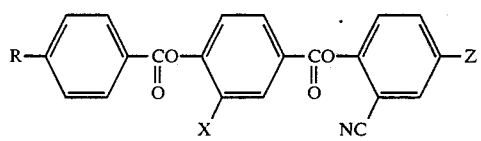
(VII)

wherein R and Z are as defined above and X represents F or Cl.

The present invention resides, in a second aspect, in (8) a liquid crystal composition having at least two components at least one of which is selected from 2-cyano-4-halogenophenyl substituted-benzoates set forth in the above item (1).

An embodiment of the above item (8) consists in the following item (9):

(9) A liquid crystal composition according to the above item (8) wherein said liquid crystal composition is nematic and the content of 2-cyano-4-halogenophenyl substituted-benzoates in the composition is in the range of 1 to 30% by weight.

DETAILED DESCRIPTION OF THE PREFERRED EMBODIMENTS

Representative examples of the compounds of the present invention will be illustrated in Examples mentioned later.

The compounds of the present invention may be prepared as follows: First the corresponding carboxylic acid chlorides are prepared and then reacted with 2-cyano-4-halogenophenols in the presence of pyridine to obtain the objective compounds. This is illustrated by the following equation:

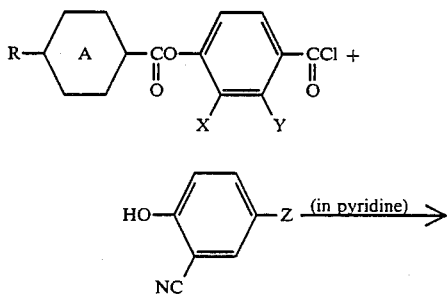
(I)

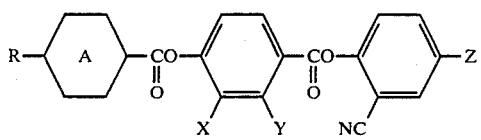
-continued wherein

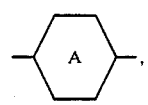

X, Y and Z are as defined above.

2-Cyano-4-halogenophenols used herein may be prepared by dehydrating 5-halogenosalicylaldoximes with acetic anhydride. The details will be described later in Examples.

Since the compounds of the present invention have high melting points, they alone are scarcely used for liquid crystal display elements, but they have a superior compatibility, a relatively low viscosity and a value of dielectric anisotropy $\Delta\epsilon$ of about $-4$, that is, a large absolute value thereof for negative $\Delta\epsilon$ values; hence when the compounds of the present invention are blended with other nematic liquid crystals such as those of phenyl cyclohexanecarboxylate esters, phenyl benzoate esters, phenylmetadioxanes, phenylpyrimidines or the like, it is possible to obtain liquid crystal compositions of a negative dielectric anisotropy having superior specific properties and usable for quest-host type display elements. Namely, when the compounds of the present invention are added, it is possible to notably reduce the threshold voltage of display elements using the resulting compositions. Further, they are usable as an additive in liquid crystal compositions for two-frequent addressing scheme as well as multiplex drive which has recently been noted.

The liquid crystal compositions of the present invention are characterized by containing therein at least one member of the compounds of the present invention in an amount of 1 to 30% by weight, preferably 5 to 15% by weight. If the content of the compounds of the present invention exceeds 30% by weight, the lower limit temperature of the liquid crystal phase region of the compositions rises, which is unpractical. If the content is less than 1%, the addition effect of the compounds of the present invention is insufficient.

As for other liquid crystal compounds which may be blended with the compositions of the present invention, the above-mentioned nematic liquid crystals of phenylcyclohexanes, phenyl cyclohexanecarboxylates, phenyl benzoates, phenylmetadioxane derivatives, phenylpyrimidine derivatives, etc. are preferable. Further, nematic liquid crystal compositions of a negative dielectric anisotropy composed of these liquid crystal compounds are preferably used. Liquid crystal compositions composed of the above compositions and one member or more of 2-cyano-4-halogenophenyl substituted-benzoates of the formula (I) have a negative dielectric anisotropy and a large absolute value thereof and are much superior as a material for liquid crystal display devices.

The present invention will be described in more detail by way of Examples, but it should not be construed to be limited thereto.

In addition, crystalline-nematic phase transition point and nematic-isotropic liquid phase transition point are hereinafter abbreviated to C-N point and N-I point, respectively.

EXAMPLE 1

2-Cyano-4-fluorophenyl 4-(trans-4-hexylcyclohexylcarbonyloxy)benzoate (1) Preparation of 2-cyano-4-fluorophenol 5-Fluorosalicylaldoxime (20.2 g, 0.13 mol) was dissolved in acetic anhydride (100 ml), followed by refluxing for 5 hours, distilling off acetic anhydride under reduced pressure after completion of the reaction, adding to the remaining oily material, a solution of KOH (20 g) dissolved in water (100 ml) and ethanol (100 ml), heating the mixture at 80° C. for 2 hours, allowing to cool down to room temperature, adding 6N-hydrochloric acid (50 ml) and water (200 ml) to deposit crystals, filtering the crystals, and recrystallizing from methanol (30 ml) to obtain acicular crystals (15.6 g). M.p. 121°~122° C.

(2) Esterification

2-Cyano-4-fluorophenol (1.5 g, 11 mmols) obtained in the above (1) was dissolved in dry pyridine (5 ml), followed by adding a solution of 4-(trans-4-hexylcyclohexylcarbonyloxy)benzoyl chloride (3.9 g, 11 mmols) dissolved in dry toluene (10 ml), and reacting on heating at 60° C. for 3 hours. The reaction mixture was added to water (100 ml) after completion of the reaction, followed by separating the toluene layer, washing the toluene layer with 6N—HCl, then with 2N—NaOH aqueous solution, and further with water, drying the toluene layer over anhydrous sodium sulfate, distilling off toluene from the toluene solution, and recrystallizing the remaining solids from acetone to obtain the objective 2-cyano-4-fluorophenyl 4-(trans-4-hexylcyclohexylcarbonyloxy)-benzoate (3.6 g, yield 72%). This product had a C-N point of 83.8° C. and a N-I point of 122.8° C.

EXAMPLES 2~31

Example 1 was repeated except that 4-(trans-4-hexylcyclohexylcarbonyloxy)benzoyl chloride and 2-cyano-4-fluorophenol were respectively replaced by the corresponding carboxylic acid chlorides and 2-cyano-4-halogenophenols, to prepare compounds of the formula (I) shown in Table 1. Their phase transition points are also shown in Table 1 together with those of Example 1. (The parentheses ( ) in the column of N-I point indicate that the phase transition is monotropic.)

TABLE 1

| Example | R | A | X | Y | Z | M.p. or C-N point | N-I point |
|---|---|---|---|---|---|---|---|
| 1 | C6H13 | (cyclohexyl) | H | H | F | 83.8 | 122.8 |
| 2 | C6H13 | (cyclohexyl) | H | H | Cl | 111.3 | 161.6 |
| 3 | C5H11 | (cyclohexene) | H | H | F | 84.8 | 121.4 |
| 4 | C5H11 | (cyclohexene) | H | H | Cl | 67.7 | 142.5 |
| 5 | C3H7O | (cyclohexene) | H | H | F | 94.3 | — |
| 6 | C3H7O | (cyclohexene) | H | H | Cl | 108.0 | — |
| 7 | C3H7 | (cyclohexyl) | H | F | F | 114.6 | 119.0 |
| 8 | C3H7 | (cyclohexyl) | H | F | Cl | 139.2 | 157.4 |
| 9 | C4H9 | (cyclohexyl) | H | F | F | 102.6 | 122.5 |
| 10 | C5H11 | (cyclohexyl) | H | F | F | 118.0 | 121.8 |
| 11 | C5H11 | (cyclohexyl) | H | F | Cl | 137.1 | 152.1 |
| 12 | C4H9 | (cyclohexyl) | H | Cl | F | 120.4 | — |
| 13 | C5H11 | (cyclohexyl) | H | Cl | F | 114.4 | — |

TABLE 1-continued

| Example | R | A (in formula I) | X | Y | Z | M.p. or C-N point | N-I point |
|---|---|---|---|---|---|---|---|
| 14 | C5H11 | cyclohexane | H | Cl | Cl | 114.7 | (110.6) |
| 15 | C5H11 | cyclohexene | H | Cl | F | 82.5 | (64.1) |
| 16 | C5H11 | cyclohexene | H | Cl | Cl | 101.6 | (90.0) |
| 17 | C3H7O | cyclohexene | H | Cl | F | 143.7 | (99.3) |
| 18 | C3H7O | cyclohexene | H | Cl | Cl | 144.7 | (126.3) |
| 19 | C5H11 | cyclohexane | F | H | F | 116.5 | 134.0 |
| 20 | C5H11 | cyclohexane | F | H | Cl | 149.0 | 170.0 |
| 21 | C3H7 | cyclohexane | F | H | F | 117.0 | 134.4 |
| 22 | C3H7 | cyclohexane | F | H | Cl | 155.8 | 177.6 |
| 23 | C3H7 | cyclohexane | Cl | H | F | 115.0 | 119.2 |
| 24 | C3H7 | cyclohexane | Cl | H | Cl | 147.6 | 168.0 |
| 25 | C4H9 | cyclohexene | F | H | F | 112.0 | (90.7) |
| 26 | C5H11O | cyclohexane | F | H | F | 84.3 | 129.7 |
| 27 | C5H11O | cyclohexane | F | H | Cl | 117.2 | 159.7 |
| 28 | C4H9 | cyclohexane | Cl | H | F | 108.4 | — |
| 29 | C4H9 | cyclohexane | Cl | H | Cl | 132.0 | (107.0) |
| 30 | C4H9O | cyclohexane | Cl | H | F | 90.2 | — |
| 31 | C4H9O | cyclohexene | Cl | H | Cl | 87.6 | — |

EXAMPLES 32~38

A nematic liquid crystal composition of ester compounds (A) consisting of

 10.4% by weight,

 10.3% by weight,

 21.1% by weight,

 19.8% by weight,

 21.0% by weight, and

 17.4% by weight had a N-I point of 62.8° C., a dielectric anisotropy value Δε of −1.0 and a viscosity at 20° C. of 18.5 cp. To this composition was added a commercially available dyestuff G-224 (made by E. Merck) in 1% by weight, followed by filling the resulting composition in a cell to prepare a guest-host cell. Its threshold voltage was measured to give 3.80 V.

Next, 2-cyano-4-fluorophenyl 4-(trans-4-hexylcyclohexylcarbonyloxy)benzoate of Example 1 of the present invention (10% by weight) was added to the above liquid crystal composition A (90% by weight) to prepare a liquid crystal composition, which had a N-I point of 67.3° C., a dielectric anisotropy value Δε of −1.2 and a viscosity at 20° C. of 27.2 cp. To this composition was similarly added the dyestuff G-224 in 1% by weight to prepare a guest-host type liquid crystal cell, followed by measuring its threshold voltage to give 3.25 V, that is, the voltage notably lowered as compared with the above value.

Similarly, to the liquid crystal composition A (90% by weight) were added the respective compounds of Examples 6, 7, 13, 17, 19 and 24, each in 10% by weight, to prepare liquid crystal compositions and color display elements, followed by measuring the specific properties of the respective compositions. The results are shown in Table 2 together with those of Example 32. In any of the cases, the threshold votages notably lowered. Further, the absolute values of Δε increased.

| Example | Compound of formula (I) added to composition (A) | N-I point (°C.) | Δε | Viscosity (20° C.) (cp) | Threshold voltage of composition containing G-224 (1%) (V) |
| --- | --- | --- | --- | --- | --- |
| 32 | Compound of Ex. 1 | 67.3 | −1.2 | 27.2 | 3.25 |
| 33 | Compound of Ex. 6 | 54.2 | −1.1 | 27.9 | 3.40 |
| 34 | Compound of Ex. 7 | 65.8 | −3.0 | 24.0 | 2.50 |
| 35 | Compound of Ex. 13 | 64.8 | −1.3 | 29.7 | 3.10 |
| 36 | Compound of Ex. 17 | 52.0 | −1.2 | 27.2 | 3.25 |
| 37 | Compound of Ex. 19 | 72.8 | −3.2 | 26.0 | 2.50 |
| 38 | Compound of Ex. 24 | 64.6 | −1.2 | 28.3 | 3.25 |
| — | Liquid crystal composition A (control) | 62.8 | −1.0 | 18.5 | 3.80 |

What we claim is:

1. A 2-cyano-4-halogenophenyl substituted-benzoate expressed by the formula

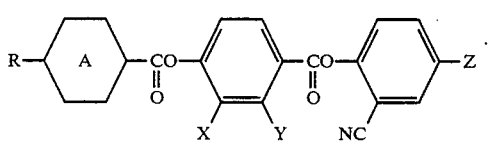 (I)

wherein R represents an alkyl group or an alkoxy group each of 1 to 10 carbon atoms;

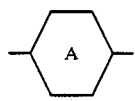

represents

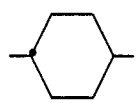

or

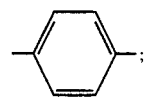

X and Y each represent H or a halogen atom of F or Cl and at least one of X and Y is necessarily H; and Z represents a halogen atom of F or Cl.

2. A 2-cyano-4-halogenophenyl 4-(trans-4-substituted cyclohexylcarbonyloxy)benzoate according to claim 1 and expressed by the formula

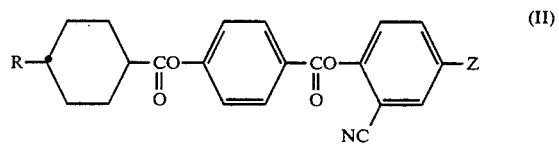 (II)

wherein R and Z are as defined in claim 1.

3. A 2-cyano-4-halogenophenyl 4-(4-substituted benzoyloxy)-benzoate according to claim 1 and expressed by the formula

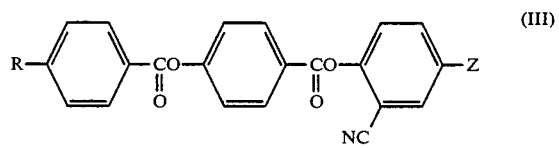 (III)

wherein R and Z are as defined in claim 1.

4. A 2-cyano-4-halogenophenyl 2-halogeno-4-(trans-4-substituted cyclohexylcarbonyloxy)benzoate according to claim 1 and expressed by the formula

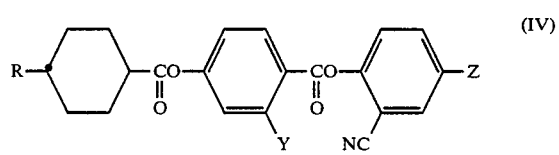 (IV)

wherein R and Z are as defined in claim 1 and Y represents F or Cl.

5. A 2-cyano-4-halogenophenyl 2-halogeno-4-(4-substituted benzoyloxy)benzoate according to claim 1 and expressed by the formula

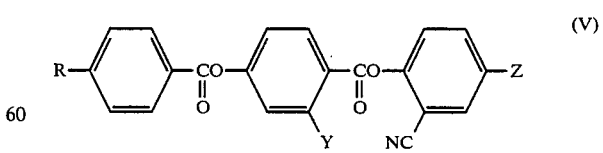 (V)

wherein R and Z are as defined in claim 1 and Y represents F or Cl.

6. A 2-cyano-4-halogenophenyl 3-halogeno-4-(trans-4-substituted cyclohexylcarbonyloxy)benzoate according to claim 1 and expressed by the formula

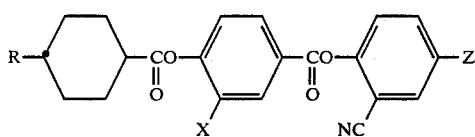

wherein R and Z are as defined in claim 1 and X represents F or Cl.

7. A 2-cyano-4-halogenophenyl 3-halogeno-4-(4-substituted benzoyloxy)benzoate according to claim 1 and expressed by the formula

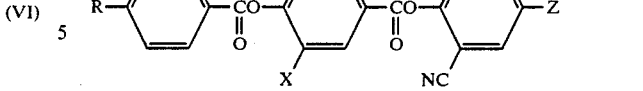

wherein R and Z are as defined in claim 1 and X represents F or Cl.

8. A liquid crystal composition having at least two components at least one of which is selected from the 2-cyano-4-halogenophenyl substituted-benzoates set forth in claim 1.

9. A liquid crystal composition according to claim 8 wherein said liquid crystal composition is nematic and the content of 2-cyano-4-halogenophenyl substituted-benzoates in the composition is in the range of 1 to 30% by weight.

* * * * *